US011337862B2

(12) United States Patent
Zopf et al.

(10) Patent No.: US 11,337,862 B2
(45) Date of Patent: May 24, 2022

(54) EAR SPLINT TO CORRECT CONGENITAL EAR DEFORMITIES

(71) Applicant: The Regents of The University of Michigan, Ann Arbor, MI (US)

(72) Inventors: David Zopf, Ann Arbor, MI (US); Kevin Green, Saint Joseph, MI (US); Kyle Vankoevering, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 385 days.

(21) Appl. No.: 16/332,453

(22) PCT Filed: Sep. 15, 2017

(86) PCT No.: PCT/US2017/051700
§ 371 (c)(1),
(2) Date: Mar. 12, 2019

(87) PCT Pub. No.: WO2018/053219
PCT Pub. Date: Mar. 22, 2018

(65) Prior Publication Data
US 2021/0282974 A1    Sep. 16, 2021

Related U.S. Application Data

(60) Provisional application No. 62/395,451, filed on Sep. 16, 2016.

(51) Int. Cl.
*A61F 5/01*    (2006.01)
*A61F 5/058*    (2006.01)
*A61F 11/20*    (2022.01)

(52) U.S. Cl.
CPC .......... *A61F 11/202* (2022.01); *A61F 5/0102* (2013.01); *A61F 5/05891* (2013.01); *A61F 2220/0025* (2013.01)

(58) Field of Classification Search
CPC ........ A61F 11/008; A61F 11/06; A61F 11/08; A61F 11/12; A61F 11/14; A61F 5/102;
(Continued)

(56) References Cited

U.S. PATENT DOCUMENTS 4,881,616 A * 11/1989 Janssen ................ H04R 25/607
181/129
6,517,557 B1   2/2003 Sorribes
(Continued)

FOREIGN PATENT DOCUMENTS

CN    203693851 U    7/2014
KR    101216388 B1   12/2012
(Continued)

OTHER PUBLICATIONS

Manu Rathee and Renu Kundu. "Magnet-Retained Prophylactic Appliance for Post-Excisional Pressure Therapy and Custom-Made Acrylic Therapeutic Pressure Appliance for Auricular Keloid: A Clinical Report." Journal of Surgical Technique & Case Report, vol. 6, Issue 1 (2014), p. 29-32.
(Continued)

*Primary Examiner* — Jerrah Edwards
*Assistant Examiner* — Ashley N. Coggins
(74) *Attorney, Agent, or Firm* — Harness, Dickey & Pierce, P.L.C.

(57) ABSTRACT

An ear splint for an ear is provided having a central portion having an exterior surface defining a first topology that is configured to dwell within an anterior scaphoid section of an ear, and a wing portion extending from the central portion and integrally formed therewith and at least partially sur-
(Continued)

rounding an outer periphery of the central portion. The wing portion includes an exterior surface defining a second topology and is configured to be positioned along a postauricular area of the ear. The first magnetic device is disposed in the central portion and the second magnetic device is disposed in the wing portion. The magnetic retention feature exert a magnetic attractive force between the central portion and the wing portion such that at least a portion of the exterior surface of the central portion and at least a portion of the exterior surface of the wing portion contact the ear.

14 Claims, 6 Drawing Sheets

(58) Field of Classification Search
CPC ........ A61F 2210/009; A61F 2220/0025; A61F 2250/0004; A61F 2250/0082; H04R 1/10; H04R 1/105; H04R 2225/021; H04R 2225/0213; H04R 2225/0216; H04R 25/607; H04R 25/02; H04R 1/1008; A44C 7/004; A44C 7/005; A44C 7/009
See application file for complete search history.

(56) References Cited

U.S. PATENT DOCUMENTS

| | | | |
|---|---|---|---|
| 7,093,600 B2 | 8/2006 | Sorribes | |
| 7,302,071 B2* | 11/2007 | Schumaier | H04R 25/606 381/151 |
| 8,167,942 B2 | 5/2012 | Byrd et al. | |
| 8,491,510 B2 | 7/2013 | Byrd et al. | |
| 8,715,347 B2 | 5/2014 | Servell et al. | |
| 9,173,762 B2 | 11/2015 | Case et al. | |
| 10,154,935 B1* | 12/2018 | Ales | A61F 5/30 |
| 10,362,411 B2* | 7/2019 | Riemer | H04R 25/65 |
| 2008/0086067 A1 | 4/2008 | Hay et al. | |
| 2009/0030358 A1 | 1/2009 | Byrd et al. | |
| 2014/0188158 A1 | 7/2014 | Servell et al. | |
| 2015/0051639 A1 | 2/2015 | Case et al. | |
| 2015/0073262 A1* | 3/2015 | Roth | A61B 5/055 600/411 |
| 2015/0382123 A1* | 12/2015 | Jobani | H04R 1/1058 700/98 |
| 2016/0057552 A1* | 2/2016 | Kure | G06T 17/00 345/420 |

FOREIGN PATENT DOCUMENTS

| | | |
|---|---|---|
| WO | 2009014908 A1 | 1/2009 |
| WO | 2010093371 A1 | 8/2010 |

OTHER PUBLICATIONS

Loyola University Health System. "Silicone Ear Looks Just Like the Real Thing." Science Daily. Mar. 19, 2009. <www.sciencedaily.com/releases/2009/03/090318104334.htm>.

Kit Eaton. "Thanko Magnetic Earring-Clip Earphones Can Make You Look like a Pirate" Gizmodo. Sep. 19, 2008. <https://gizmodo.com/thanko-magnetic-earring-clip-earphones-can-make-you-loo-5052121>.

Byrd, H. Steve et al., Ear molding in newborn infants with auricular deformities, Plastic and Reconstructive Surgery, Oct. 2010, vol. 126, pp. 1191-1200.

* cited by examiner

_Fig-3B_

_Fig-4_

EAR SPLINT TO CORRECT CONGENITAL EAR DEFORMITIES

CROSS-REFERENCE TO RELATED APPLICATIONS

This application is a U.S. National Phase Application under 35 U.S.C. 371 of International Application No. PCT/US2017/051700 filed on Sep. 15, 2017. This application claims the benefit of U.S. Provisional Application No. 62/395,451, filed on Sep. 16, 2016. The entire disclosures of all of the above applications are incorporated herein by reference.

FIELD

The present disclosure relates to congenital ear deformities and, more particularly, to an ear splint to correct congenital ear deformities.

BACKGROUND AND SUMMARY

This section provides background information related to the present disclosure which is not necessarily prior art. This section also provides a general summary of the disclosure, and is not a comprehensive disclosure of its full scope or all of its features.

It is well known that children can be born with ear malformations, which can often be the result of genetics, viral infections, and/or lack of blood supply or toxins during pregnancy. It is estimated that 6-45% of children are born with some form of congenital ear defect. There are various forms of ear malformation that include microtia (underdeveloped ear), anotia (missing an ear), protruding ears (ears that stick out more than 2 cm), Stahl's ear (pointed shape), cryptotia (cartilage buried beneath the skin), and ear tags (accessory cartilage). Some malformations can also have effect on proper vision in children, as a child with an improperly formed ear cannot wear glasses. For children with ear deformities or malformations, there is dramatic psychosocial harm done to the child most often due to severe teasing and bullying.

Ear deformities are traditionally treated in two ways: surgery for ear reconstruction and ear molding on newborns. Surgery is often costly, and the risks of anesthesia and other complications usually defer surgery until the child reaches at least six to ten years of age. Unfortunately, surgical solutions after lead to outcomes that lack in both appearance and functionality.

Therefore, if it is possible, ear modeling is preferred over surgical solutions. It is understood that an infant's ear is malleable in the first several weeks of life and, thus, deformities can potentially be corrected before surgical intervention is needed.

Ear molding in newborns can only be done with outer ear deformities where none of the ear is missing but is just misshaped. Currently, the most commonly-used molding technique is a mold 100, known as the EARWELL as illustrated in FIGS. 1A-1D. As can be seen from the figures, the mold is a large device that covers the entire ear and surrounding area. Adhesive tape is typically used to retain the mold in position on the infant patient. It is also noted that a large area of shaving is required to allow for copious adhesive necessary to maintain the device in place. Unfortunately, the device, due to its size and attachment method (i.e. adhesive), is susceptible to dislodgement and other complications. Highly complex base and inserts prevents the possibility for replacement by the patient family. The entire device is excessively large, poorly tolerated, and may be prone to displacement.

According to the principles of the present teachings, an ear splint to correct congenital ear deformities is provided that is both low-profile and comfortable. In some embodiments, the ear splint of the present teachings is particularly suitable for use on malleable infant ears. Ideally, the ear splint can be manufactured using a 3D printing technique to ensure proper configuration, comfort, and patient-specific fitment. This results in a patient-specific ear splint that is rapidly produced, at low-cost, and that avoids the need for skin adhesive that can lead to complications and skin breakdown.

Furthermore, according to the principles of the present teachings, an ear splint for an ear is provided having a central portion having an exterior surface defining a first topology that is configured to dwell within an anterior scaphoid section of an ear, and a wing portion extending from the central portion and integrally formed therewith and at least partially surrounding an outer periphery of the central portion. The wing portion includes an exterior surface defining a second topology and is configured to be positioned along a postauricular area of the ear. The first magnetic device is disposed in the central portion and the second magnetic device is disposed in the wing portion. The magnetic retention feature exert a magnetic attractive force between the central portion and the wing portion such that at least a portion of the exterior surface of the central portion and at least a portion of the exterior surface of the wing portion contact the ear.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 6A-6C illustrates a modular molding apparatus for ear splint production, wherein

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As described herein, ear malformations exist on a spectrum from slightly noticeable asymmetry and deformity to complete absence of the ear. When the cartilaginous component of the ear is partially or completely missing the current gold standard is use of costal cartilage for reconstruction. Malformations seen when the cartilage is present, but deformed, including cup ear deformity, Stahl ear deformity, prominotia, and low-grade microtia, are often unaddressed. This may be due to paucity of available treatment options. Additionally, the patient and caregiver may decide surgical intervention and associated risks do not outweigh the benefits of restoring normal shape to the ear.

The use of ear splints to conservatively correct selected ear malformations without surgery, secondary to malleability of the infant ear cartilage, has been described with reports of success. However, the current devices on the market are highly expensive, cumbersome for the family and surgeon to use, and questionably tolerated by the patient. The most established device, the EarWell (see FIGS. 1A-1D), costs approximately $3,500 per ear, necessitates a physician to remove and replace in situations of skin breakdown and splint displacement, and is extremely bulky.

According to the principles of the present disclosure, an ear splint is provided that is capable of overcoming the disadvantages of the prior art. In some embodiments, the present teachings provide an ear splint can comprise a three-dimensional (3D) structure that is based on three-dimensional scanning and, in some embodiments, printing modalities that result in an extremely cost-effective, easy to use, and more aesthetically pleasing ear splint device for ear malformations and other uses.

In some embodiments, an ear splint 10 is provided having a central portion 20 and a wing portion 22 generally surrounding the central portion 20. It should be understood that the particular size and shape of ear splint 10 can vary depending on the associated size and shape of the ear of the patient, therefore the description and figures should not be regarded as limiting unless otherwise claimed. In some embodiments, central portion 20 is sized and shaped to be inserted within the concha and/or scaphoid portion of the ear. Likewise, in some embodiments, wing portion 22 is sized and shaped to surround central portion 20 and extend about an exterior portion of the ear, such as along the post auricular and anterior scaphoid area. In this way, wing portion 22 can be opposingly-spaced relative to central portion 20.

It should be appreciated that, in some embodiments, an exterior surface 24 of central portion 20 defines a shape that is substantially similar to a desired internal, post-formation topology of the ear. Likewise, in some embodiments, an exterior surface 26 of the wing portion 22 defines a shape that is substantially similar to a desired external, post-formation topology of the ear. In some embodiments, the shape of central portion 20 and wing portion 22 is determined by a clinician prior to treatment, is a mirror shape of the scanned shape of a patient's properly formed ear, and/or is selected from a library or database of potential ear shapes. To this end, each of central portion 20 and wing portion 22 can define a contour having a complex, multi-surface and/or multi-faceted shape, as illustrated in the figures, that is similar to a final or incremental topological shape of the ear. More particularly, in unilateral ear deformities, a multipod photographic scan, laser scan, or DICOM base imaging scan can be used to obtain topologic data from the normal ear, then mirror and serve as a template for the patient specific ear splint. In the case of bilateral ear deformity, normative data could be used or computer aided virtual repair of ear deformities could allow for template production.

In some embodiments, ear splint 10 can be sized and shaped to be generally positioned within the ear and generally surround the ear such that ear splint 10 does not extend beyond the helix or other outermost elevational portion of the ear. In some embodiments, ear splint 10 is made of a material, such as soft silicone material, that is likely to minimize pressure necrosis.

Figure 1A:
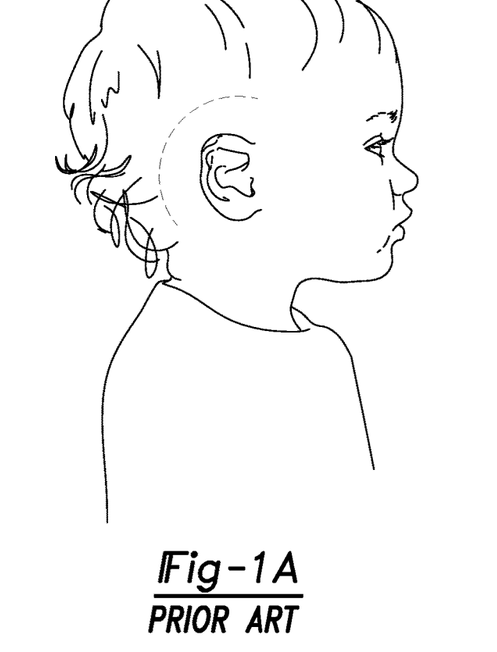
FIG. 1 illustrates a conventional mold device according to the principles of the prior art.
Figure 1B:
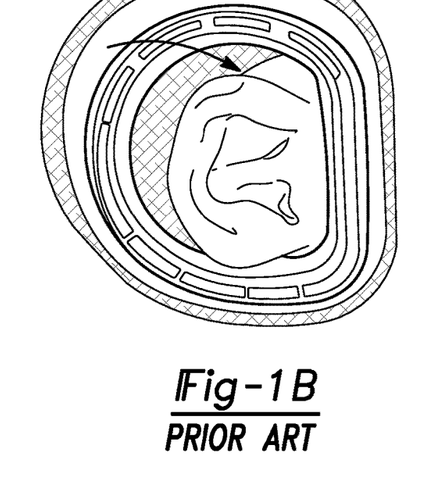
Figure 1C:
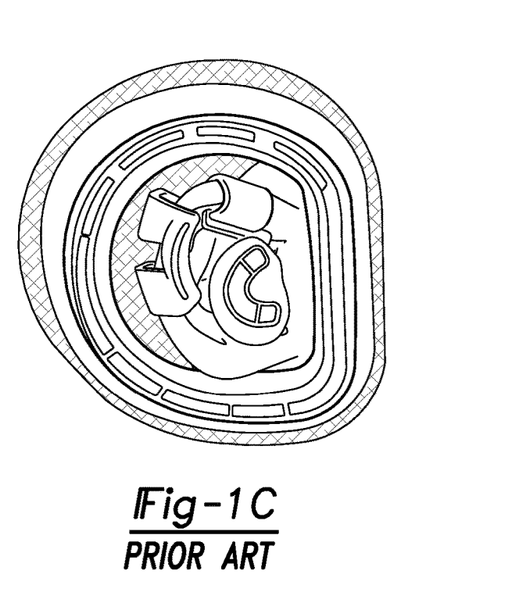
Figure 1D:
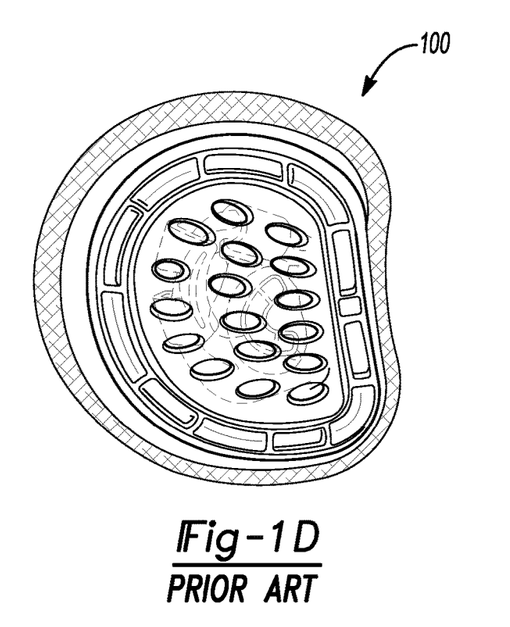
Figure 2A:
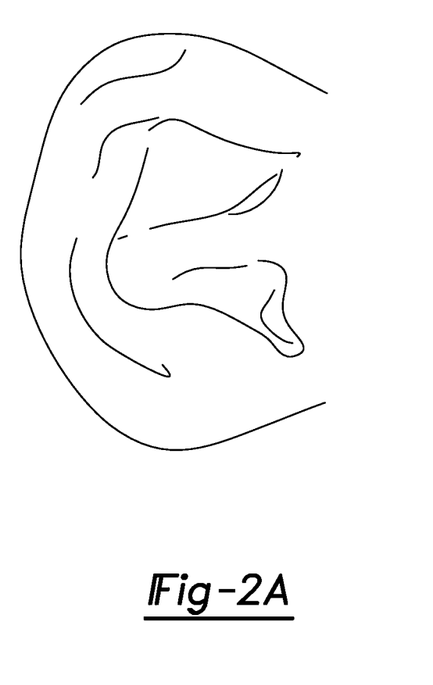
FIG. 2A is a photograph of an ear exhibiting malformaties.
Figure 2B:
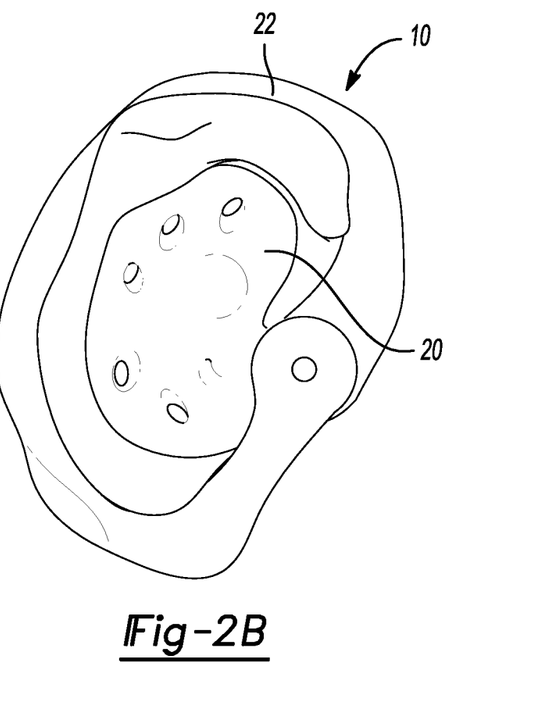
FIG. 2B illustrates a 3D printed ear splint according to the principles of the present disclosure attached to the ear of FIG. 2A.
Figure 3A:
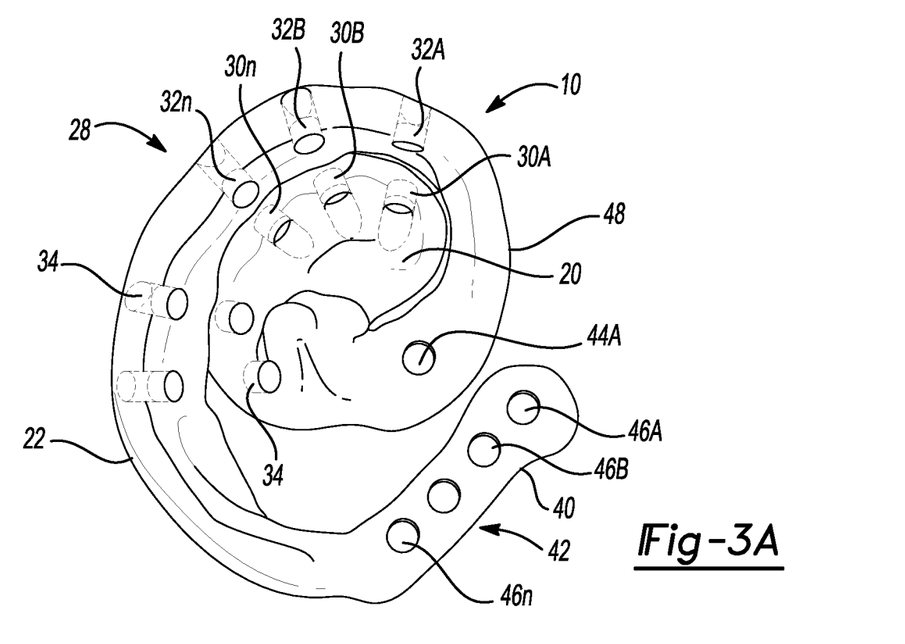
FIG. 3A is a front view illustrating the ear splint according to the principles of the present teachings having an anterior securement strap with adjustable magnetic array allowing for growth of the patient.
Figure 3B:
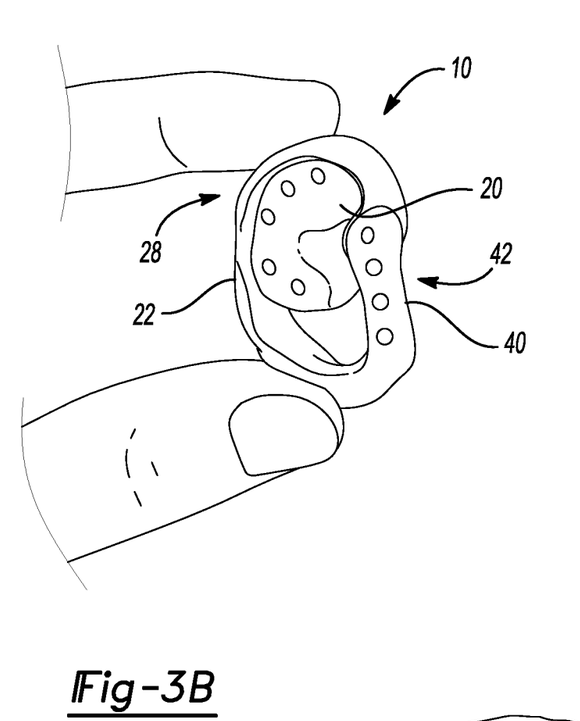
FIG. 3B is a photograph illustrating the ear splint according to the principles of the present teachings.
Figure 4:
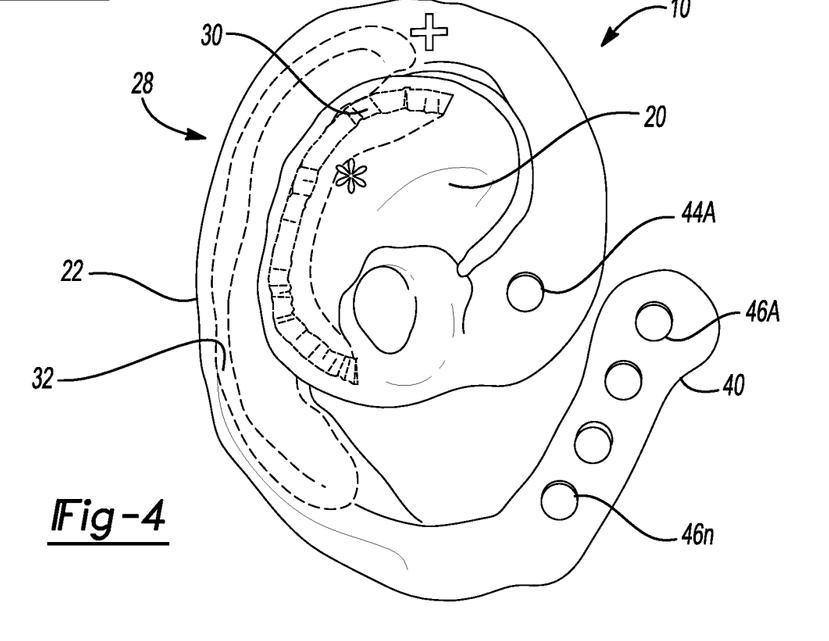
FIG. 4 is a front view of an ear splint according to some embodiments of the present teachings having a variable magnetic component, in the form of a crescent shaped magnet, in the postauricular wing portion and the anterior scaphoid central portion.
Figure 5:
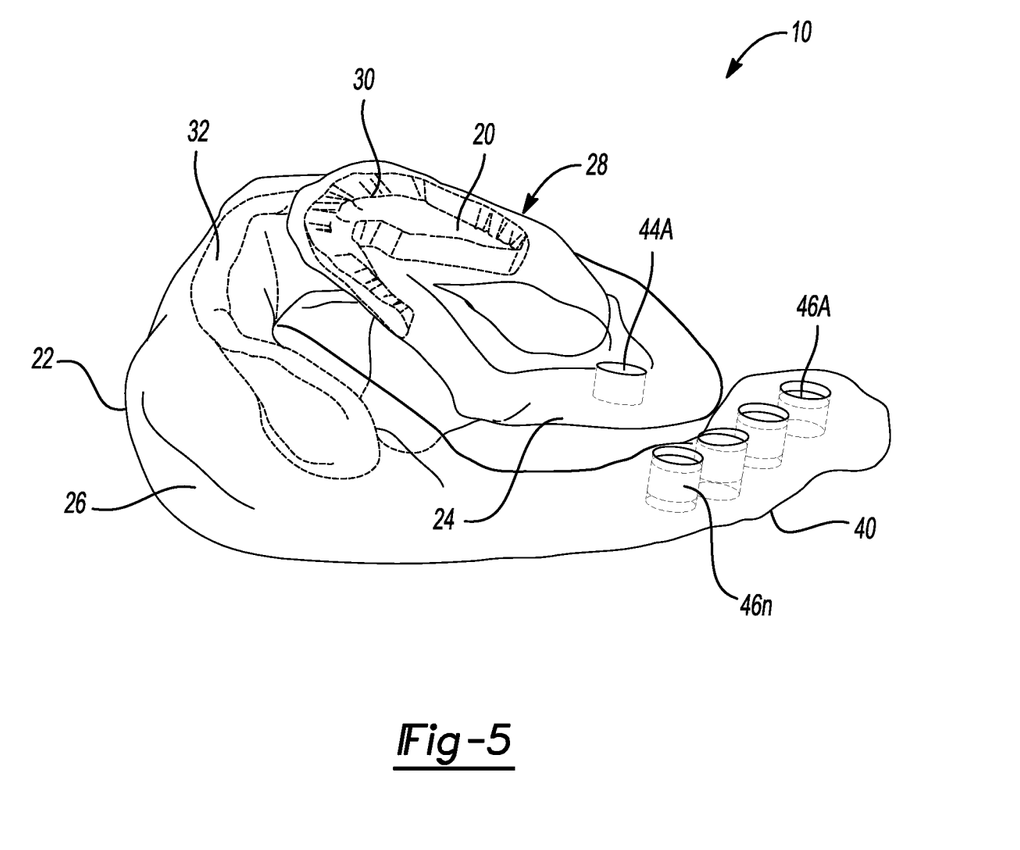
FIG. 5 is a perspective view of the ear splint of FIG. 4.

In some embodiments, ear splint 10 can comprise one or more magnetic retention features 28. In some embodiments, magnetic retention features 28 can comprise opposingly-spaced magnetically attracting pairs of magnets 30, 32. More particularly, as illustrated in FIGS. 2-5 and 7-8, ear splint 10 can comprise a first pair of magnets 30A-32A, a second pair of magnets 30B-32B, and an n-th pair of magnets 30n-32n radially disposed in central portion 20 and wing portion 22. Magnetic retention features 28 are configured to exert a magnetic coupling force between central portion 20 and wing portion 22 to provide a force sufficient to grasp and urge the malleable cartilage of the ear to form into a shape that is substantially similar to the exterior surface of the central portion 20 and the wing portion 22. Magnets 30, 32 can be disposed in bores 34 formed in central portion 20 and wing portion 22 or otherwise coupled thereto, such as through adhesive, fastening, overmolding, and the like. However, as illustrated in FIGS. 4-5, in some embodiments, magnetic retention feature 28 can comprise a single pair of magnets 30, 32 that extend along a circumferential portion of central portion 20 and wing portion 22 in opposing relation to each other.

The opposingly-spaced arrangement of magnetic retention features 28 (and, specifically, magnets 30, 32) serves to aid in the precise alignment of central portion 20 and wing portion 22 to define an ear molding volume between central portion 20 and wing portion 22. Exterior surface 24 of central portion 20 and exterior surface 26 of wing portion 22 together define the ear molding volume that will serve to shape the malleable cartilage of the ear through exertion of formation pressure thereon. By securing the device with the multi magnet design, the need for skin adhesive/glue is mitigated and/or eliminated. Furthermore, by preventing the need for adhesive there is no need for shaving. This arrangement further minimizes and/or eliminates skin breakdown and wound issues, and provides improved overall patient and family experience.

Minimization of skin irritation is further achieved by the precise placement of a silicone housing for magnets 30, 32. Magnets 30, 32 can be inset within bore 34 to prevent direct contact of the magnet with the skin, thereby permitting on the soft silicone material of central portion 20 and wing portion 22 to touch the skin of the patient. Moreover, by distributing the force generated by the magnetic pressure of magnets 30, 32 to all of central portion 20 and wing portion 22, adequate cartilage shaping support is imparted while avoiding risk of pressure necrosis. The magnetic distribution can be tailored to the deformity and would range from 1 pair to 10 pair, generally.

In some embodiments, a distal end portion 40 of wing portion 22 comprises one or more magnetic securement features 42. In some embodiments, magnetic securement feature 42 can comprise one or more opposingly-spaced magnetically attracting securement pairs 44, 46. Magnetic securement feature 42 can be used to retain and/or secure ear splint 10 in engagement with the patient's ear. To this end, in some embodiments as illustrated, magnetic securement feature 42 can comprise magnet 44A disposed in a proximal portion 48 of wing portion 22 generally adjacent where wing portion 22 extends from central portion 20. One or more magnets 46A-n can be disposed along distal end portion 40 of wing portion 22 such that magnet 44A and magnet 46A-n are magnetically joinable. It should be understood that any one of magnets 46A-n can be magnetically joined to magnet 44A to permit adjustment of ear splint 10 on the patient. This adjustment can permit continued use of ear splint 10 as the ear and/or patient grows. It should be understood one or more magnets 44A can be used with one or more magnets 46A-n to permit a greater degree of adjustment.

In some embodiments, the overall design is configured to permit ear splint 10 to be positioned within the ear structures and in the post auricular crease behind the ear allowing for extremely low profile. Moreover, the simplicity of insertion of central portion 20 and wing portion 22, together with the simple attachment of magnetic retention features 28 and magnetic securement features 42, enable a parent or lay caregiver the ability to reattach ear splint 10. Ear splint 10, due to its personalize shape and low-profile design, minimize displacement while maximizing comfort to the patient. The design allows for extremely low profile noting it does not project beyond the native ear. The paired magnet design allows for precise placement, even by the novice. This additionally makes removal of the splint in several potential scenarios—parent desire for specific events, MRI, bathing—simple to perform and replace.

In some non-limiting embodiments, ear splint 10 can comprise 0.20 lbs (0.089 N) magnets, although potential magnet strengths ranging from 0.010 N to 5.0 N are within the scope of the present teachings. This strength diminishes as the soft tissue distance increases. In some embodiments, ear splint 10 defines a surface area upon which force is applied to be 220 mm^2, which would vary based on the patient size. In an exemplary embodiment employing 5 pairs of magnets, the pressure exerted is less than 2000 Pascals or 0.3 psi from the magnets.

Figure 6A:
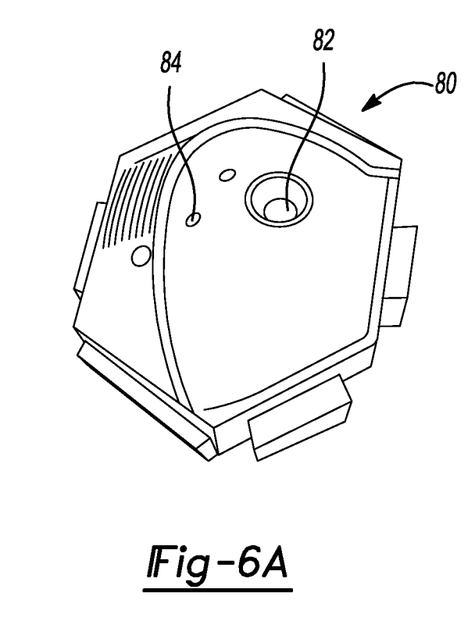
FIG. 6A is a top view illustrating a pour receptacle and smaller adjacent ventilation ports.
Figure 6B:
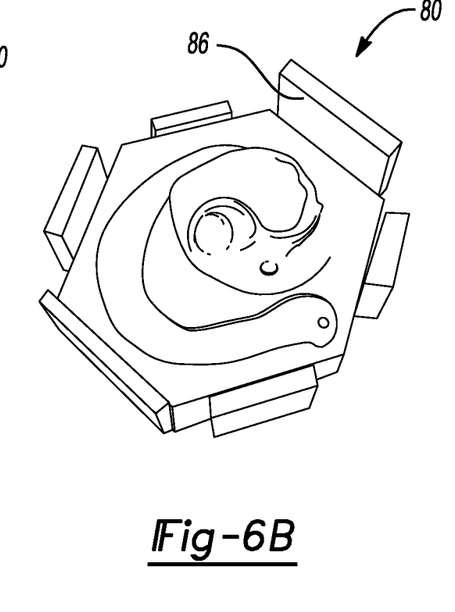
FIG. 6B illustrates opposing modules having fit tabs and ear topology design, and FIG. 6C illustrating magnet inset struts and ear topology.
Figure 6C:
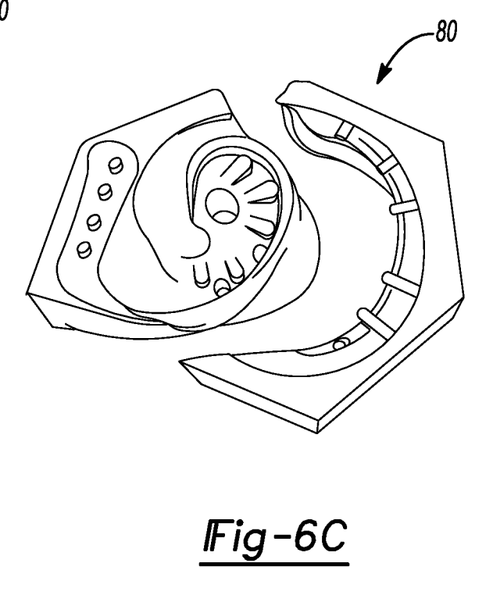

Ear splint 10 can be manufactured accordingly to any convenient method, such as 3D-printing, molding, and the like. It is preferable that ear splint 10 is made for a particular patient and/or application. However, it should be understood that many of the principles of the present teachings are applicable to mass production. Moreover, ear splint 10 can be made using a personalized mold 80, as illustrated in FIGS. 6A-6C. The mold 80 can include unique design components to enable rapid, precise manufacturing. For example, the strategically-placed pour access 82 maximizes filling of the central portion 20 of the ear splint 10, which requires the highest volume of silicone or other material.

Adjacent air vents 84 in the mold 80 allow effusion of air bubbles during the curing process. The elevated sides 86 snap the mold 80 into place to prevent silicone leakage during curing. The three-part design allows for easy disassembly of the ear mold, particularly in the narrow magnet wells.

Although the present teachings are particularly adapted and configured for use as an ear splint to aid in the proper development of malformed ears in infants, it should be understood that varying and useful embodiments and methods of use are envisioned. By way of non-limiting example, ear splint 10 can be used as a post-operative dressing for ear surgeries. One of the most common complications of ear surgeries is post-operative hematoma. The secure fit and pressure provided by the design of the magnetic ear splint may eliminate the risk of hematoma and may also improve postoperative appearance. Silicone is known to decrease scarring, hypertrophic wound healing, and keloiding.

Figure 7:
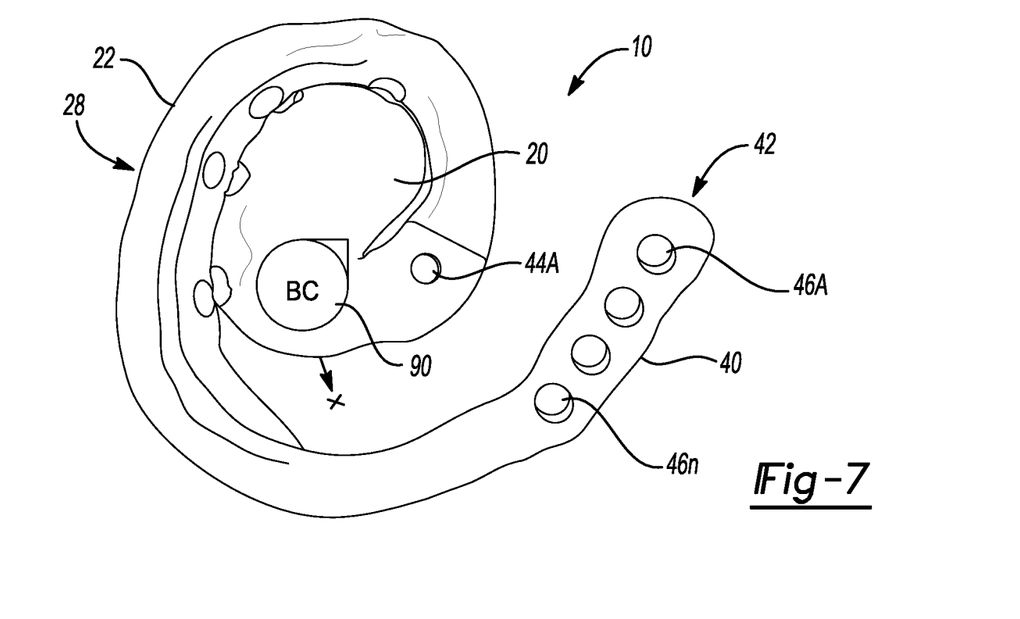
FIG. 7 is a front view illustrating the ear splint having a bone conductor hearing aid according to some embodiments.
Figure 8:
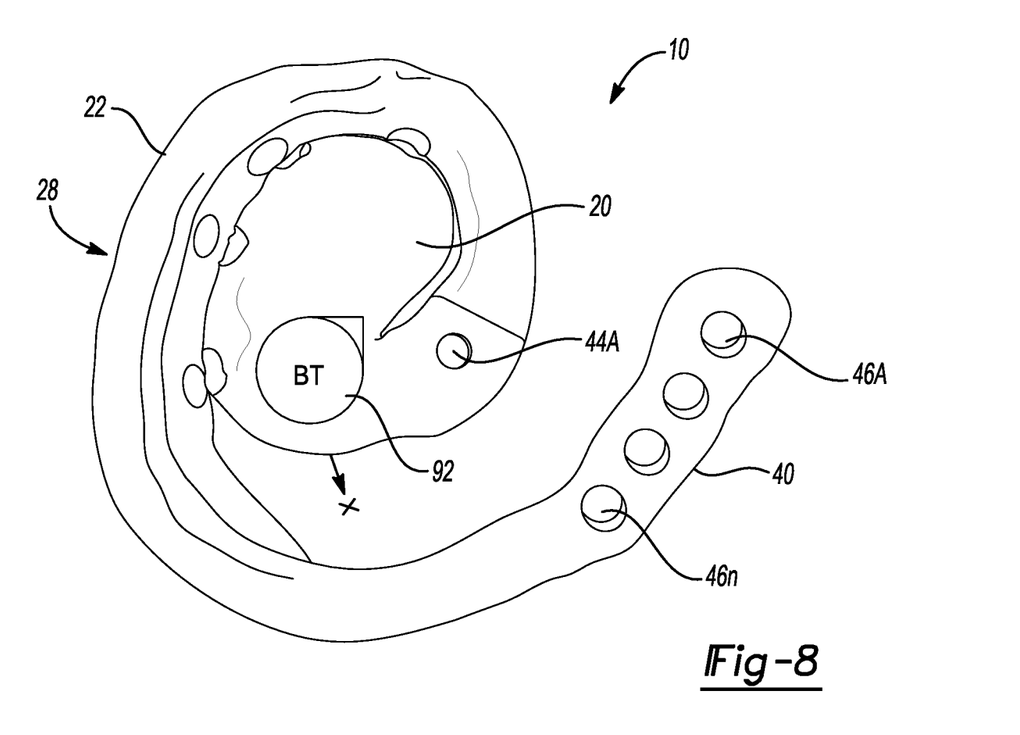
FIG. 8 is a front view illustrating the ear splint having a Bluetooth wireless transceiver or receiver.

In some embodiments, it should be understood that ear splint 10 can be used for alternative uses, such as, but not limited to, a customized earplug or headset design for any user. In such embodiments, it should be understood that the topology of central portion 20 and wing portion 22 need not define a desired post-procedure topology, but rather may merely represent a custom fit of the current ear topology without intending to manipulate or otherwise treat the ear. Instead, ear splint 10 can define a customized topology that closely (if not exactly) contours to the existing ear topology. This can be particular useful in application that require a comfortable, sealing connection to the ear, such as, but not limited to, swimming and watersport uses, firearms applications, aviation application, or other applications where uses traditionally need sealing and/or hearing protection. Still further, as illustrated in FIGS. 7 and 8, ear splint 10 can comprise a bone conduction-type hearing aid 90 (FIG. 7) and/or a Bluetooth type wireless transmitting system 92 (FIG. 8). To this end, ear splint 10 may serve as a platform and housing for Bluetooth receiver and speaker. Similarly, in bone conduction applications, optimal deliver of the bone conduction may include the central portion 20 or the wing portion 22.

With the intended high level of ear feature specificity, circumferential ear design, and magnetic securement, fit is intended to be highly secure and comfortable. This design facilitates maintenance of placement making the device well suited for exercise and activity.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An ear splint for an ear, the ear splint comprising:
a central portion having an exterior surface defining a first topology, the central portion configured to dwell within an anterior scaphoid section of an ear;
a wing portion extending from the central portion and integrally formed therewith, the wing portion at least partially surrounding an outer periphery of the central portion, the wing portion having an exterior surface defining a second topology, the wing portion configured to be positioned along a postauricular area of the ear;
a magnetic retention feature having a first magnetic device and a second magnetic device being magnetically attractive to each other, the first magnetic device being disposed in the central portion, the second magnetic device being disposed in the wing portion, the magnetic retention feature exerting a magnetic attractive force between the central portion and the wing portion such that at least a portion of the exterior surface of the central portion and at least a portion of the exterior surface of the wing portion contact the ear; and
a magnetic securement feature to retain the ear splint in engagement with the ear, the magnetic securement feature having at least one pair of securement magnets, a first of the at least one pair of securement magnets being disposed in a proximal end of the wing portion and a second of the at least one pair of securement magnets being disposed in a distal end of the wing portion, the at least one pair of securement magnets being magnetically attractive to each other to retain the distal end of wing portion to the proximal end of wing portion about the postauricular area of the ear.

2. The ear splint according to claim 1 wherein the first topology and the second topology define a complementary shape of a desired final shape of the ear.

3. The ear splint according to claim 1 wherein at least one of the first topology and the second topology is determined from a scan.

4. The ear splint according to claim 3 wherein the scan is a multipod photographic scan, laser scan, or DICOM base imaging scan.

5. The ear splint according to claim 1 wherein at least one of the first topology and the second topology is determined from a database.

6. The ear splint according to claim 1 wherein the central portion and the wing portion are each limited to an elevation height that is less than a maximum elevation height of the ear.

7. The ear splint according to claim 1 wherein the magnetic retention feature comprises a plurality of pairs of first magnetic devices and second magnetic devices each being magnetically attractive to the other of the pair, each of the plurality of first magnetic devices being disposed at radial locations about the central portion, each of the plurality of second magnetic devices being disposed at radial locations along the wing portion.

8. The ear splint according to claim 7 wherein each of the plurality of pairs is operably positioned to maintain a predetermined alignment of the central portion and the wing portion.

9. The ear splint according to claim 1 wherein the magnetic securement feature comprises a plurality of securement magnets extending along the distal end of the wing portion and magnetically attractive to the first of the securement magnets disposed in the proximal end of the wing portion.

10. The ear splint according to claim 1 wherein at least one of the central portion and the wing portion are made of a silicone material.

11. The ear splint according to claim 1 wherein at least one of the first magnetic device and the second magnetic device is disposed within a bore to inhibit direct physical contact with the ear.

12. The ear splint according to claim 1, further comprising:
   a wireless receiving device disposed within the central portion.

13. The ear splint according to claim 1, further comprising:
   a bone conducting device disposed within the central portion.

14. The ear splint according to claim 1 wherein the central portion and the wing portion are made using a 3D printing protocol.

* * * * *